US006823207B1

(12) United States Patent
Jensen et al.

(10) Patent No.: US 6,823,207 B1
(45) Date of Patent: Nov. 23, 2004

(54) INTEGRATED FLUOROSCOPIC SURGICAL NAVIGATION AND IMAGING WORKSTATION WITH COMMAND PROTOCOL

(75) Inventors: Vernon Thomas Jensen, Draper, UT (US); Gregory Scott Lloyd, Boise, ID (US); Larry E. Harrawood, Sandy, UT (US); Barry Keith Hanover, Salt Lake City, UT (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 09/649,071

(22) Filed: Aug. 26, 2000

(51) Int. Cl.[7] .............................. A61B 5/05; H05G 1/08
(52) U.S. Cl. ........................................ 600/427; 378/91
(58) Field of Search ................................ 600/428, 427, 600/424, 407; 378/91, 21, 29; 709/228; 328/131, 128

(56) References Cited

U.S. PATENT DOCUMENTS

| | | | | |
|---|---|---|---|---|
| 5,091,926 A | * | 2/1992 | Horton et al. ............... | 378/114 |
| 5,186,174 A | | 2/1993 | Schlondorff et al. ....... | 128/653.1 |
| 5,251,127 A | | 10/1993 | Raab ...................... | 364/413.13 |
| 5,305,203 A | | 4/1994 | Raab ...................... | 364/413.13 |
| 5,383,454 A | | 1/1995 | Bucholz ................... | 128/653.1 |
| 5,389,101 A | | 2/1995 | Heilbrun et al. ........... | 606/130 |
| 5,494,034 A | | 2/1996 | Schlondorff et al. ....... | 128/653.1 |
| 5,603,318 A | | 2/1997 | Heilbrun et al. ........... | 128/630 |
| 5,676,673 A | | 10/1997 | Ferre et al. ............... | 606/130 |
| 5,748,767 A | | 5/1998 | Raab ........................ | 382/128 |
| 5,772,594 A | | 6/1998 | Barrick ..................... | 600/407 |
| 5,794,356 A | | 8/1998 | Raab ........................ | 33/503 |
| 5,800,352 A | | 9/1998 | Ferre et al. ............... | 600/407 |
| 5,803,089 A | | 9/1998 | Ferre et al. ............... | 128/897 |
| 5,829,444 A | | 11/1998 | Ferre et al. ............... | 128/897 |
| 5,873,822 A | | 2/1999 | Ferre et al. ............... | 600/407 |
| 5,891,035 A | * | 4/1999 | Wood et al. ............... | 600/437 |
| 5,907,395 A | | 5/1999 | Schulz et al. ............. | 356/139.03 |
| 5,920,395 A | | 7/1999 | Schulz ..................... | 356/375 |
| 5,951,475 A | * | 9/1999 | Gueziec et al. ............ | 600/425 |
| 6,230,043 B1 | * | 5/2001 | Johnson .................... | 360/18 |
| 6,470,207 B1 | * | 10/2002 | Simon et al. .............. | 600/426 |

(List continued on next page.)

FOREIGN PATENT DOCUMENTS

| | | | | |
|---|---|---|---|---|
| DE | 198 07 884 | * | 9/1999 | ........... A61B/5/103 |
| WO | WO 0047103 | | 8/2000 | |

OTHER PUBLICATIONS

Partial European Search Report for EP 01 30 7077, dated Nov. 10, 2003.
"Computer Assisted Medical Interventions," 4527 IEEE Engineering in Medicine and Biology 14 (1995), Cinquin et al.

*Primary Examiner*—Shawna J Shaw
(74) *Attorney, Agent, or Firm*—McAndrews, Held & Malloy, Ltd; Peter J. Vogel; Michael A. Dellapenna

(57) ABSTRACT

A medical diagnostic imaging system includes an X-ray source and X-ray detector, sensors tracking a position of at least one of a surgical instrument and the X-ray detector, and an integrated imaging and navigation workstation. The integrated imaging and navigation workstation includes at least one processor executing fluoroscopic imaging based on an output of the X-ray detector and navigation tracking of positions of a surgical instrument and positions of an X-ray detector with respect to a coordinate system. The integrated imaging and navigation workstation also includes an input receiving surgical instrument tracking signals from the sensors, an input receiving detector tracking signals from the sensors, and a display for displaying fluoroscopic images with a displayed instrument superimposed. In particular, one or more relations of the displayed instrument with respect to the fluoroscopic image (e.g., coordinate location and rotation) corresponds to the relation of the surgical instrument to the patient.

18 Claims, 6 Drawing Sheets

U.S. PATENT DOCUMENTS

2002/0021828 A1 * 2/2002 Papier et al. ................ 382/128
2002/0191814 A1 * 12/2002 Ellis et al. ................... 382/103
2003/0028091 A1 * 2/2003 Simon et al. ................ 600/407
2003/0208122 A1 * 11/2003 Melkent et al. ............. 600/426
2004/0015077 A1 * 1/2004 Sati et al. .................... 600/427
2004/0076259 A1 * 4/2004 Jensen et al. ................. 378/91
2004/0087852 A1 * 5/2004 Chen et al. .................. 600/407

* cited by examiner

700

INTEGRATED FLUOROSCOPIC SURGICAL NAVIGATION AND IMAGING WORKSTATION WITH COMMAND PROTOCOL

BACKGROUND OF THE INVENTION

The preferred embodiments of the present invention relate to surgical navigation systems and techniques. In particular, the preferred embodiments of the present invention relate to an integrated surgical navigation system and fluoroscopic X-ray system.

Medical imaging techniques including X-ray, CAT (Computerized Axial Tomography), MRI (Magnetic Resonance Imaging), and ultrasound are well established. These techniques provide an examining physician with high resolution images useful for subsequent detailed study and diagnosis. Recently, however, surgical navigation techniques have been proposed that use pre-operative images for improving inter-operative visualization of patient anatomy. To that end, one or more of the pre-operative images are displayed for the surgeon during an operation, with a surgical tool superimposed on the image in the correct location.

The navigational challenges associated with using pre-operative images during surgery include establishing a known coordinate system with respect to the patient, registering pre-operative images in the coordinate system, and tracking surgical tool movement through the coordinate system. In the past, navigation systems, attempting to meet these challenges, were developed as separate and independent add-on systems to be connected to separate and independent imaging systems. The add-on navigation systems were designed as separate navigation units, and generally did not adhere to a standard or consistent communications protocol for communicating with the imaging system.

As a result, prior navigation systems 1) required significant additional floor-space (in an already overcrowded operating room environment), 2) did not support high speed digital data transfer to the imaging system, and 3) had no bi-directional command and control interface with the imaging system. The lack of bi-directional command and control with the imaging system make it difficult, if not impossible, to ensure that position information from the navigation system actually corresponded to the moment in time that the image was acquired. As a result, tracking errors arise, for example, in a C-arm type X-ray system performing fluoroscopy, when the C-arm moves. The tracking error may arise during the time interval between the point in time at which image acquisition is finished and the point in time at which the navigation information was obtained. Any tracking error is undesirable in surgical navigation.

Additionally, the external output ports of prior imaging systems were generally limited to NTSC or PAL video outputs. An NTSC or PAL video output represents an immediate reduction in resolution and dynamic range in comparison with the original digital image read out of an X-ray detector (e.g., a 1024×1024 image). Thus, as a separate system, conventional navigation systems were limited to using a frame grabber connected to the imaging system output port to acquire lower resolution images for later surgical navigation. Furthermore, where DICOM was used to transfer images between the imaging system and navigation system, the DICOM overhead limited throughput to as little as one image every twelve seconds.

A need has long existed for a method and apparatus for fluoroscopic surgical navigation that addresses the problems noted above, and other problems previously experienced.

BRIEF SUMMARY OF THE INVENTION

A preferred embodiment of the present invention provides a medical diagnostic imaging system. The medical diagnostic imaging system includes an X-ray source and X-ray detector, sensors tracking a position of at least one of a surgical instrument and the X-ray detector, and an integrated imaging and navigation workstation. The integrated imaging and navigation workstation includes at least one processor executing fluoroscopic imaging based on an output of the X-ray detector and navigation tracking of positions of a surgical instrument and positions of an X-ray detector with respect to a coordinate system. The integrated imaging and navigation workstation also includes an input receiving surgical instrument tracking signals from the sensors, an input receiving detector tracking signals from the sensors, and a display for displaying fluoroscopic images with a displayed instrument superimposed. In particular, one or more relations of the displayed instrument with respect to the fluoroscopic image (e.g., coordinate location and rotation) corresponds to the relation of the surgical instrument to the patient.

Another preferred embodiment of the present invention provides a diagnostic imaging system communication protocol. The communication protocol implements bi-directional communication between a medical imaging subsystem and a medical navigational subsystem. The communication protocol includes a set of navigation subsystem to imaging subsystem messages as well as a set of imaging subsystem to navigation subsystem messages. The imaging subsystem to navigation subsystem messages include a start imaging and end imaging message. The messages may include Ping response time messages, system configuration, file request, image request, and image reply messages, as examples.

DETAILED DESCRIPTION OF THE INVENTION

Figure 1:
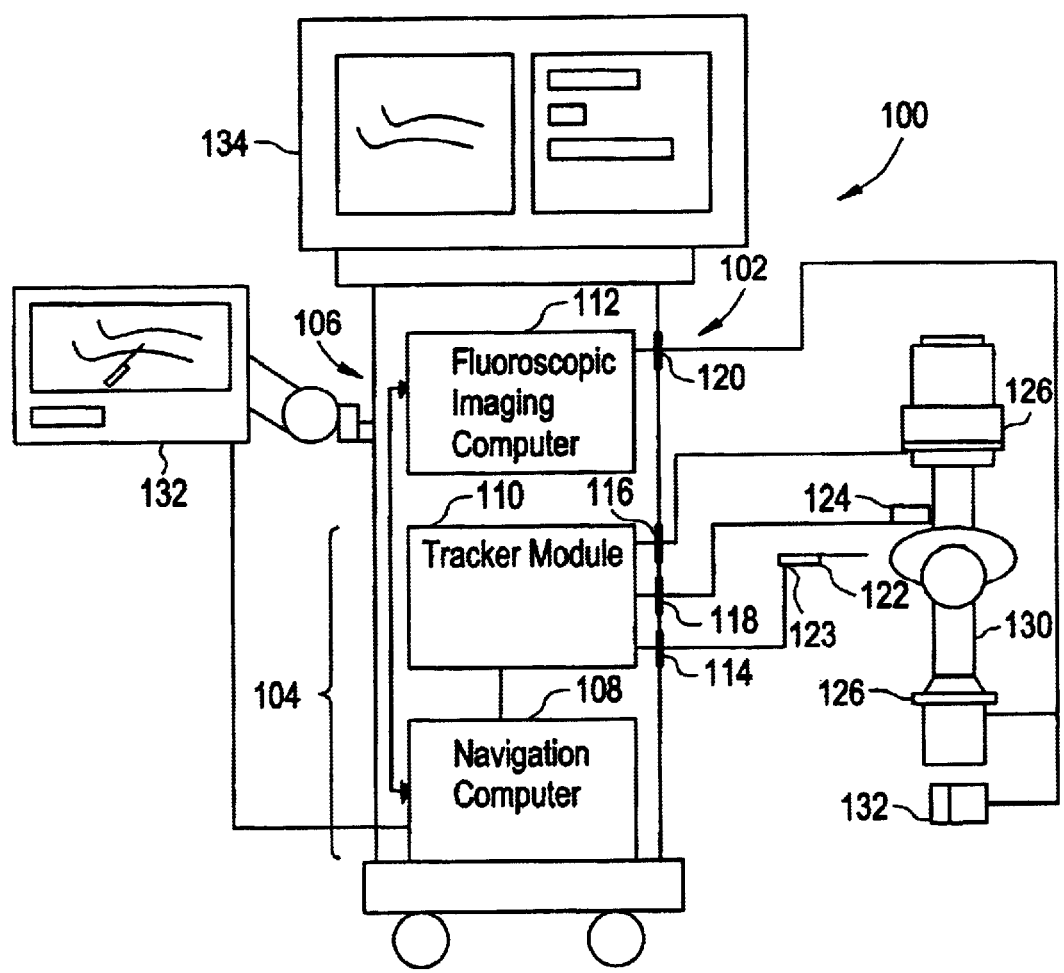
FIG. 1 shows a high level block diagram of a medical diagnostic imaging system.

FIG. 1 illustrates a block diagram of a medical diagnostic imaging system 100. The imaging system 100 includes an integrated imaging and navigation workstation 102 that in turn includes a navigation subsystem 104 and an imaging subsystem 106 (shown in FIG. 1 as a fluoroscopic imaging-subsystem). The navigation subsystem 104 includes a navigation computer 108 and a tracker module 110, while the imaging subsystem includes an imaging computer 112.

The imaging system 100 further includes a workstation surgical tool tracking sensor input port 114, a workstation X-ray-detector fixture tracking sensor input port 116, a workstation dynamic reference frame transmitter control output port 118, and a workstation X-ray exposure output port 120 (that communicates with a foot switch activated exposure module 132). The X-ray detector fixture connects to an image intensifier (or solid state flat panel detector) on the C-arm 130. The tool sensor input port 114 allows the imaging system 100 to be coupled to a tool location sensor 123 on a medical (e.g., surgical) tool 122. The medical tool 122 may be, for example, an aspirating device such as that disclosed in U.S. Pat. No. 5,873,822, an orthopedic drill, awl, or probe, and the like. The transmitter control output port 118 connects the imaging system 100 to the location transmitter 124. The detector tracking sensor input 116 allows the imaging system to receive tracking signal inputs from an X-ray detector position sensor 126 that detects the position of an image X-ray detector. The X-ray exposure output port 120 allows the imaging system 100 to communicate with the exposure module 132 and to read images from the X-ray detector. The exposure module 132, in turn, provides a physician with foot switch activated X-ray exposure control.

The imaging system 100 also provides a navigation displays 132 (attached to a movable display arm) for displaying images output by the navigation subsystem 104 as well as an imaging display 134 for displaying images output by the imaging subsystem 106. The navigation subsystem 104, imaging subsystem 106, and displays 132–134 are preferably placed in a self contained mobile cart system.

The sensors 123 and 126 output pulsed signals representative of the sensor's location. The tracker module 110 implements coordinate determination from location pulses received via the detector tracking sensor input 116 and the tool sensor input 114 using the predetermined coordinate system typically associated with the location transmitter 124 and referenced to patient anatomy. The coordinates may include, for example, x, Y, and Z locations as well as roll, pitch, and yaw angles.

To the end, the location transmitter 124 may be implemented, for example, as a field generator that includes three orthogonally disposed magnetic dipoles (e.g., current loops or electromagnets). Electromagnetic fields generated by each of the dipoles are distinguishable from one another in phase, frequency, time division multiplexing, and the like. The near-field characteristics of the electromagnetic fields may be used for coordinate determination as generally described, for example, in U.S. Pat. No. 4,054,881, which is incorporated by reference herein in its entirety. Alternate embodiments of the location transmitter 124 may employ ultrasonic or optical fields. Alternatively, more than one location transmitter 124 may be used in a coordinate determination system based on triangulation of signals. Commercially available position detection units, including the 3 Space® Fastrak™ system from Polhemus, Incorporated of Colchester, Vt. may also be used.

Additional details of coordinate determination using a location transmitter and associated reception sensors may be found in U.S. Pat. No. 5,873,822.

Figure 2:
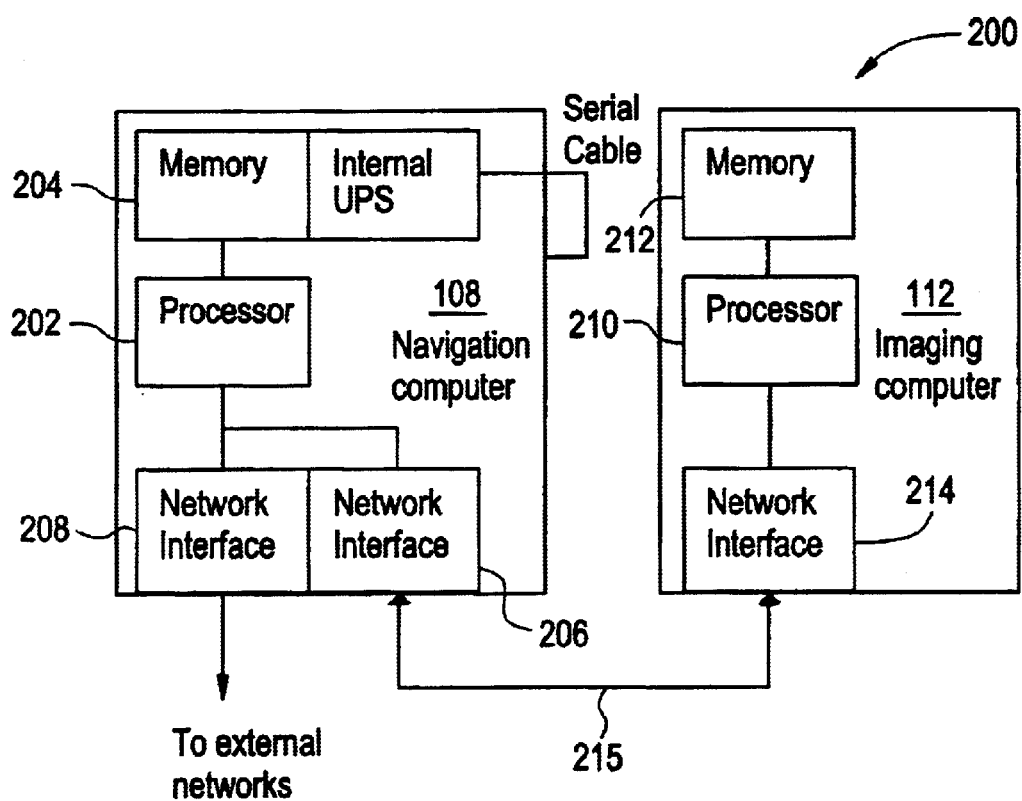
FIG. 2 illustrates a block diagram of an integrated fluoroscopic surgical navigation and imaging workstation.

Turning next to FIG. 2, that figure presents a block diagram of an integrated fluoroscopic surgical navigation and imaging workstation 200. The workstation 200 includes the navigation computer 108 and the imaging computer 112. The navigation computer includes a navigation processor 202, program/data memory 204, and a navigation network interface 206. The navigation network interface 206 implements a high speed digital communication interface (e.g., two or more 1024×1024×16 images per second). The images may be cropped in accordance with a circular blanking window to approximately 980×980 resolution. In other words, the navigation computer 108 receives full resolution digital images directly from the imaging computer 112 without the need for NTSC or PAL image grabbers, conversion to NTSC or PAL format, or the associated loss of resolution and dynamic range. The navigation network interface 206 may be, for example, a 100BaseT Ethernet network card. The navigation computer is preferably implemented as a Sun UltraSparc 10 running Solaris 2.6 with an un-interruptable power supply (UPS). A second network interface 208 may be provided in the navigation computer 108 for forwarding packets to other destinations.

The imaging computer 112 includes the imaging processor 210, program/data memory 212, and imaging network interface 214. The imaging computer 112 is preferably implemented as an Intel x86 platform, for example, a Pentium™ processor based PC with 32–128 Megabytes of memory. The imaging network interface 214 is compatible with, and is generally implemented in the same manner as, the navigation network interface 206. The network interfaces 206, 208, 214 are used not only as a high speed digital communication bus, but also as a command and control bus that the imaging computer 112 and the navigation computer 108 may use to coordinate their functions (particularly image acquisition with coordinate determination as noted below).

Note that tool configuration updates may be performed using a floppy disk (or other storage media or TFPT protocol) interface in the imaging computer 112. In addition, the operating system and application software may be accomplished using a CDROM interface with keyboard and mouse control. Operating system and application software updates may be accomplished through the imaging network interface 214 using FTP, telnet, the Sun Sparc™ pkgadd command, and the like. The network addresses assigned to the network interfaces 206, 208, and 214 may be reconfigured in a similar fashion using telnet, the vi editor, and ifconfig, as examples.

The workstation 200 shown in FIG. 2 provides a private network for the imaging computer 112 and the navigation computer 108 to communicate. The imaging computer 112 and the navigation computer 108 communicate, preferably, using a socket-based command protocol over TCP/IP. The private network is assigned an Internet Protocol (IP) address which is allocated strictly to private networks (e.g. 192.168.0.0/24) and is generally not routed over the Internet. Hence, each workstation 200 shipped can use the same internal network address if desired. Note also that DICOM Ethernet traffic from the imaging computer 112 may pass through the navigation computer 108, which forwards the DICOM traffic to the second network interface 208.

The workstation 200 may access external networks by using a Network Address Translation (NAT) at the navigation computer 108 to translate the IP address of the packets coming from the workstation 200 to a host IP address assigned to the system. In addition, a firewall may be implemented with an IP filter to prevent unnecessary external network traffic from reaching the private network between the Navigation Computer and Workstation. The firewall may be configured, for example, to block all inbound traffic from an external network except for ping, traceroute, FTP, and telnet commands. In addition, external outbound initiated traffic is allowed only for the duration of the required connection.

In one embodiment, the workstation 200 sets the IP address to "network.1" (e.g., 192.168.0.1) for the imaging computer 112 and the net mask to 255.255.255.0. The workstation 200 also sets the default route to "network.2" (e.g. 192.168.0.2, assigned to the navigation computer 108). In other words, the navigation network interface 206 is preferably assigned an IP address of "network 2" or 192.168.0.2. The second network interface 208 (connected to external networks) is assigned an IP address allocated by a third party. The imaging network interface 214 is preferably assigned an IP address of 192.168.0.1 and is translated to and from the third party specified IP address.

On boot-up and when changed, the workstation 200 preferably sends the following to the navigation computer 108: Host IP address and sub-net mask, Gateway Address (e.g., obtained from DICOM store, print, and query screens), Date and Time, Language Configuration (e.g., English, French, German, Spanish, or Italian).

In operation, the imaging computer 112 monitors the connection 215 through the network interfaces 206 and 214 for network protocol commands and responds synchronously. For example, the imaging computer 112 may respond to Ping requests to check the connection between the imaging computer 112 and the navigation computer 108, Request Image requests (e.g., to request transfer of the left display image from imaging computer 112 without patient information), and Request Configuration requests. The imaging computer 112 generally sends network protocol commands to the navigation computer 108 asynchronously, including a Ping command to check a connection, Imaging Begin and End commands to delineate, for example, live X-ray exposure periods, a New Exam command to tell the navigation computer 108 that the current patient is no longer valid, and an Update Patient command to update the current patient information. Thus, responses from the imaging computer 112 are generated synchronous to a predetermined timing source, while original commands may be sent asynchronously. Additionally, the imaging computer 112 monitors for File Transfer commands and responds by retrieving the appropriate file and forwarding it to the navigation computer 108.

Generally, when the navigation computer 108 is on a private network, it is not available for communication for a few seconds (e.g., 90 seconds) after the imaging computer 112 boots. During this time period, the imaging computer 112 may display an error message such as "Navigation Computer not responding, Power Off, wait 10 seconds, then Power On". If communication fails between the imaging computer 112 and navigation computer 108 after a connection is established, the imaging computer 112 may timeout, for example, after 2 seconds, close the connection between the navigation computer 108 and the imaging computer 112, and display an error message such as "Communication Failure with Navigation Computer".

Preferably, the navigation computer 108 and the imaging computer 112 have different power-down strategies. The imaging computer 112 may be powered down at any time by removing the AC power without notifying the operating system of a shutdown. Conversely, the navigation computer 108 preferably executes a shutdown procedure before removing AC power. To this end, the un-interruptible power supply (UPS) is used to hold power with battery backup while the navigation computer 108 shuts down. The UPS provides the power status on a serial port, which is used to signal the navigation computer 108 of a power loss.

Generally, the navigation computer 108 may be booted simultaneously with the imaging computer 112, a UPS background (e.g., a daemon) process shall monitor the serial port for a power loss, including imaging computers 112 power switch status. Upon receiving a power loss signal, the navigation computer 108 initiates an operating system shutdown, following which the navigation computer 108 is powered off.

The navigation computer 108 and the imaging computer 112 may be implemented using a single processor executing both navigation and imaging software. Alternatively, a multi-processor system, under the coordination of an symmetric multiprocessing operating system (e.g., Windows NT) may be used to allow a single set of processors to execute the navigation and imaging software. However, as described below, the navigation computer 108 and the imaging computer 112 may also be implemented as separate processing units, coupled together with the network interfaces 206, 214 and communicating with the diagnostic imaging system communication protocol set forth below.

Figure 3:
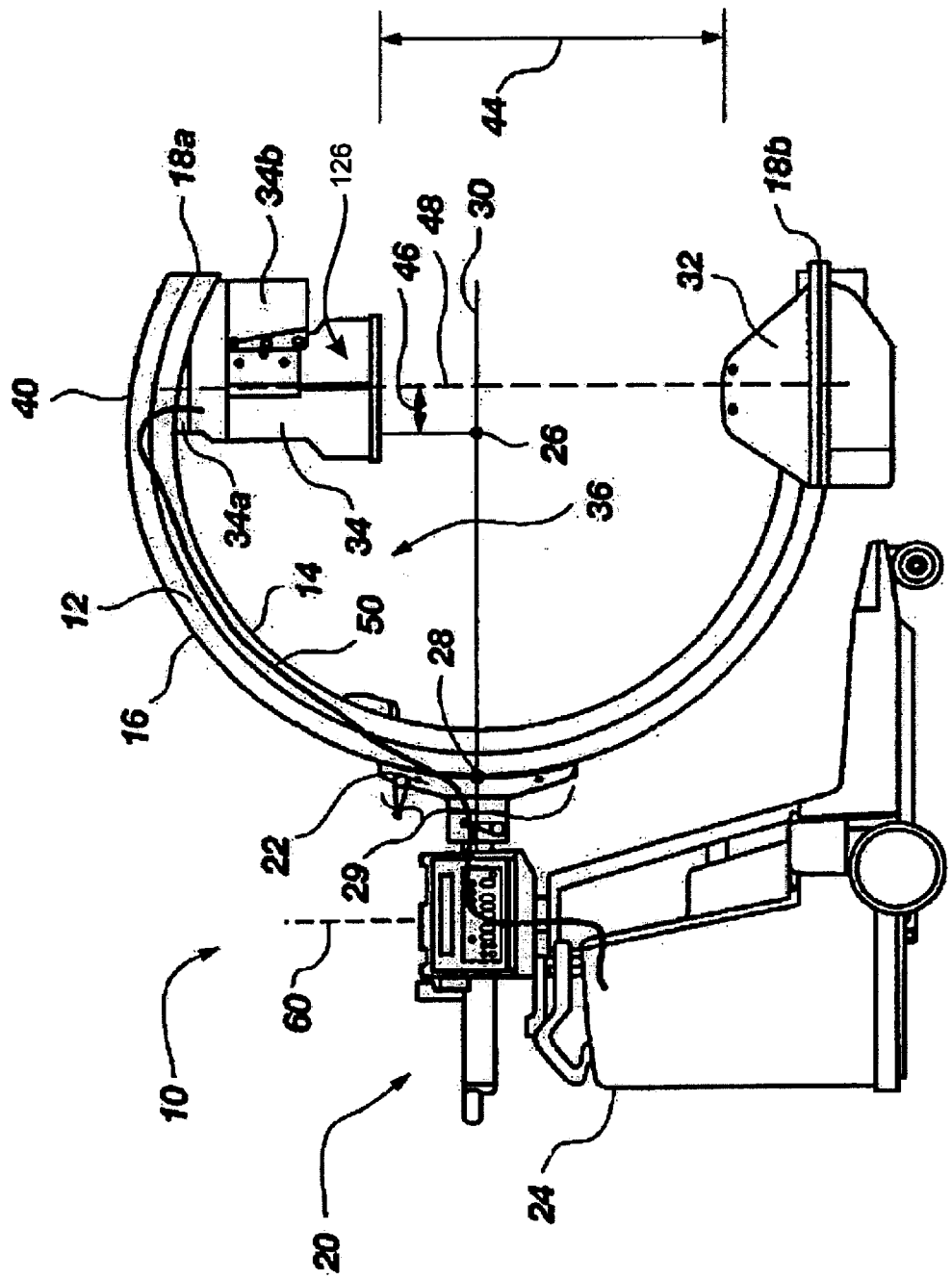
FIG. 3 shows an example of a C-arm that may be used for integrated fluoroscopic surgical navigation.

Turning next to FIG. 3, that figure shows an exemplary C-arm apparatus 10 that may be used with the medical diagnostic imaging system 100. The apparatus 10 includes a C-arm 12 having inner and outer circumferences 14 and 16, respectively, a back convex portion 40, and terminating in opposing upper and lower distal ends 18a and 18b. The C-arm 12 preferably has a uniformly circular C-shape, but may alternatively comprise any arc-shaped member.

The C-arm 12 is held in a suspended position by support means such as structure, generally designated at 20, which includes a support arm 22 mounted upon a wheeled base 24. The support arm 22 provides for rotational movement of the C-arm 12 about an axis of lateral rotation 30, either by a bearing assembly between the support arm 22 and the C-arm 12, or by the support 22 itself being rotatably mounted with respect to the base 24. The apparatus 10 may also be provided with rotational capacity for rotational movement about an axis 60.

The wheeled base 24 enables transport of the C-arm 12 from a first location to a second location. As such, the wheels of the base operate as transporting means coupled to the support structure 20 for transporting the support arm 22 and the C-arm 12 from a first location to a second location. It is often highly advantageous to be able to move X-ray equipment from one room to another conveniently. The mobile nature of the apparatus 10 as provided by the wheeled base 24 offers the advantage of increased access by patients in many different rooms of a hospital, for example.

The support arm 22 is slidably mounted to the outer circumference 16 of the C-arm 12 and the support structure 20 includes structure and mechanisms necessary to enable selective, sliding orbital motion of the C-arm about an axis of orbital rotation 26 to a selected position. The axis 26 preferably coincides with a center of curvature of the C-arm 12 and with the axis of lateral rotation 30. It will be appreciated that the sliding orbital motion causes the C-arm 12 to move through various sliding points of attachment 28 to the support arm 22. It will be appreciated that in practice, the support arm is essentially attached to the C-arm over an area 29 and not a single point, although a "point" may be a large area or a small site. The support structure 20 further includes mechanisms known in the art for laterally rotating the support arm 22 selectable amounts about an axis of lateral rotation 30 to a selected lateral position. The combination of sliding orbital motion and lateral rotation enables manipulation of the C-arm in two degrees of freedom, i.e. about two perpendicular axes. This provides a kind of spherical quality to the movability of the C-arm 12. The sliding orbital motion and lateral rotation enable an X-ray source 32 coupled to the C-arm to be moved to substantially any latitude/longitude point on a lower hemisphere of an imaginary sphere about which the C-arm is moveable.

The apparatus 10 includes an X-ray source 32 and an image receptor 34 as known generally in the X-ray diagnostic art, mounted upon opposing locations, respectively, on the C-arm 12. The X-ray detector position sensor 126 is generally located inside the camera assembly of the image receptor 34 (which may further include registration fiducials and the like that may be used to compensate for image pincushioning and other effects imposed by the image receptor). The X-ray source 32 and the image receptor 34 (including a rear portion 34a, and a power supply 34b) may be referred to collectively as the X-ray source/image receptor 32/34. The image receptor 34 can be an image intensifier or the like. The orbital and laterally rotational manipulation of the C-arm enables selective positioning of the X-ray source/image receptor 32/34 with respect to the width and length of a patient located within interior free space 36 of the C-arm 12. The sliding orbital movement of the C-arm causes the X-ray source/image receptor 32/34 to move along respective arcuate movement paths. The image receptor 34 is preferably secured to the inner circumference 14 of the C-arm 12 and the X-ray source 32 may also be secured to said inner circumference 14. A high voltage cable assembly 50 supplies power to the X-ray source/image receptor 32/34.

The mounted positions of the image receptor 34 and the C-arm 12 result in the axis of lateral rotation 30 substantially coinciding with the point of attachment 28 of the C-arm 12 to the support arm 22 for substantially any position of the C-arm 12. Thus, rotation of the support arm 22 does not introduce eccentric lateral moment-arm action so as to provide a more stabile, balanced support structure. In one preferred embodiment, the center of mass of the C-arm 12 coincides with the axis 30 for any position of the C-arm.

An additional aspect of the C-arm includes the location of a power supply 34b of the image receptor 34. By locating the power supply 34b toward the C-arm opening, the image receptor 34 and the X-ray source 32 can be moved closer to the center of curvature 26, thereby reducing the distance 46 and thus improving overall balance of the apparatus 10. Balancing is enhanced by having a distance 46 between a line of alignment 48 and the intersection of the axes 26 and 30. The line of alignment 48 refers to alignment of a central beam produced by the X-ray source 32, and the image receptor 34. Note also that for a given desired distance 44 between the X-ray source/image receptor 32/34, a larger C-shape can be used for the C-arm 12 without substantially increasing the overall machine height.

A diagnostic imaging system communication protocol is defined to implement bi-direction communication between the imaging computer 112 and the navigation computer 108. Tables 1 shows the messages provided for communication from the navigation computer 108 to the imaging computer 112.

TABLE 1

From Navigation Computer to Workstation

| Message | Data |
|---|---|
| Ping | no data |
| Request Image | no data |
| Request Configuration | no data |
| Request File | filename (e.g., using TFTP) |

Tables 2 shows the messages provided for communication from the imaging computer 112 to the navigation computer 108.

TABLE 2

From Imaging Computer To Navigation Computer

| Message | Data |
|---|---|
| Ping | no data |
| Image (e.g., Fluoro) Begin | no data |
| Image (e.g., Fluoro) End | no data |
| New Exam | no data |
| Update Patient | e.g., patient name, birth date, sex, patient ID, physician name, procedure, accession number |
| Image Reply | e.g., image width, height, bytes per pixel, endian, field of view, negation, subtraction, flip backward/upside-down, rotation, pixel data |
| Configuration Reply | e.g., system model, intensifier diameter, C-arm type, software version |
| File Reply | file data (e.g., using TFTP) |
| Language Sync | e.g., "echo FRENCH > /usr/vti/resource.file" or "sed_" (e.g., using rexec) |
| Time Sync | e.g., "date 051614502000.34" (e.g., using rexec) |
| Set IP Address | e.g., "ifconfig hme0 <customer IP> netmask <mask>" (e.g., using rexec) |
| Route Add | e.g., "route add <destination IP> -netmask <mask> <gateway IP>" (e.g., using rexec) |

Figure 4:
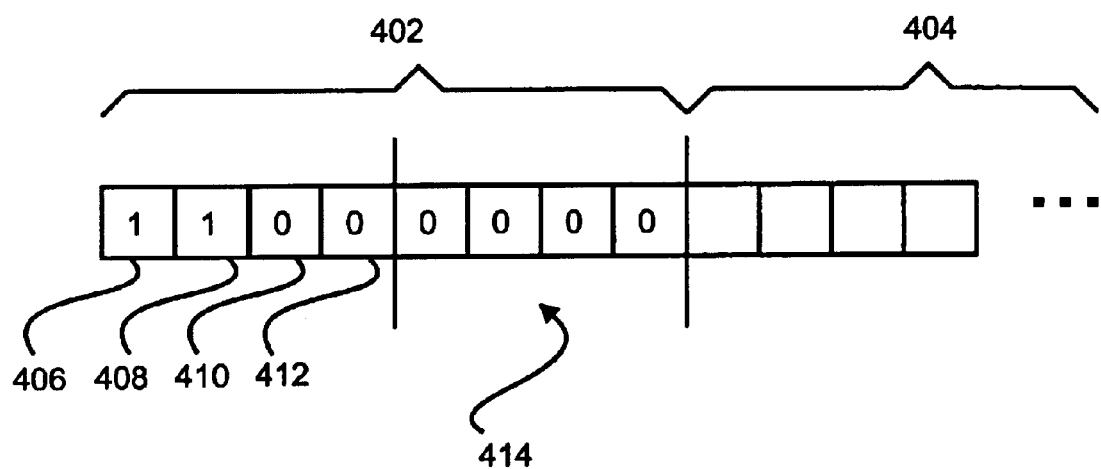
FIG. 4 shows a diagnostic imaging system communication protocol message format.
Figure 4:

With regard to FIG. 4, that figure shows a diagnostic imaging system communication protocol message format 400. The message format 400 is used with the diagnostic imaging system protocol to implement, preferably, a bi-directional connection-oriented TCP-based data transfer protocol. Once a connection is accepted and established (e.g., by monitoring port 8500), the client (i.e., message sender) and server (i.e., message receiver) threads keep the connection open. The server thread preferably blocks (i.e., waits or loops without performing other actions) waiting for the next message which will indicate a command to perform. Then, the server executes the command and returns a reply message (which may contain data) to the client. The server continues in a loop waiting for the next message.

The communication protocol generally processes one particular message at a time. That is, at the moment when a particular message is sent, the sender does not send any other message until a corresponding reply message is received. The message format 400 includes a fixed-length header 402 followed by the data section 404 associated with the message (if any). The same message header format 400 is used for the initial message and the reply.

Illustrated in FIG. 4 are a 1-byte Code field 406, a 1-byte Type field 408, a 1-byte Flag field 410, and a 1-byte Status field 412. A 4-byte Data Length field 414 is also provided. The Code field 406 and Type field 408 are defined for each message below. The Flag field 410 generally uses bit 0 as a reply flag (1: reply, 0: otherwise), bit 1 as a request flag (1: request for data, 0: otherwise), and bit 2 as an Endian indicator (1: big, 0: little). The Status field 412 provides status codes (as additionally explained below), for example, (0: OK, non-0: ERROR). The Data Length field 414 provides an unsigned 4-byte length of data to follow in the data section 404.

Figure 5:
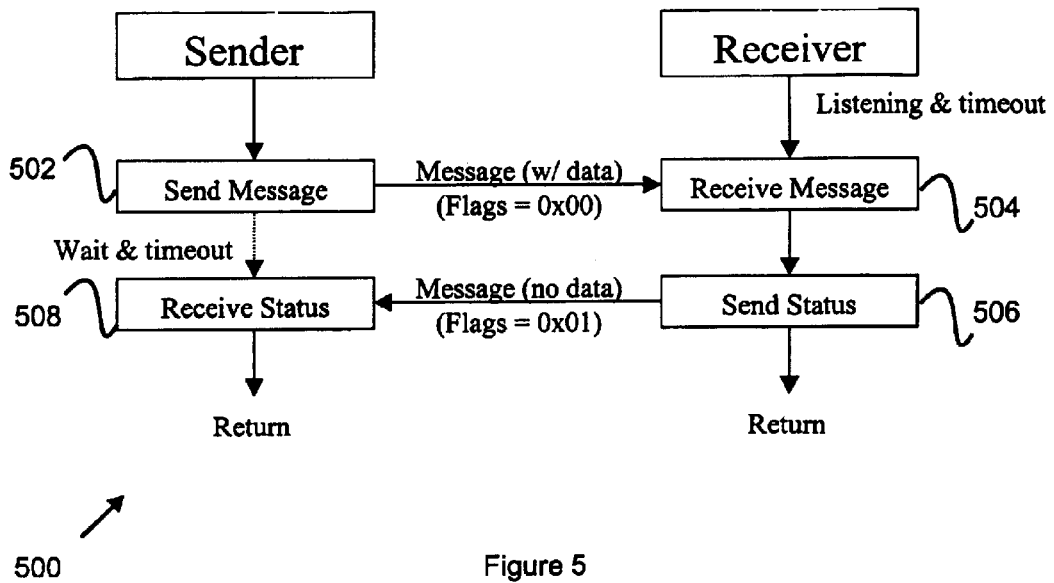
FIG. 5 illustrates a flow diagram for sending data according to a diagnostic imaging system communication protocol.
Figure 6:
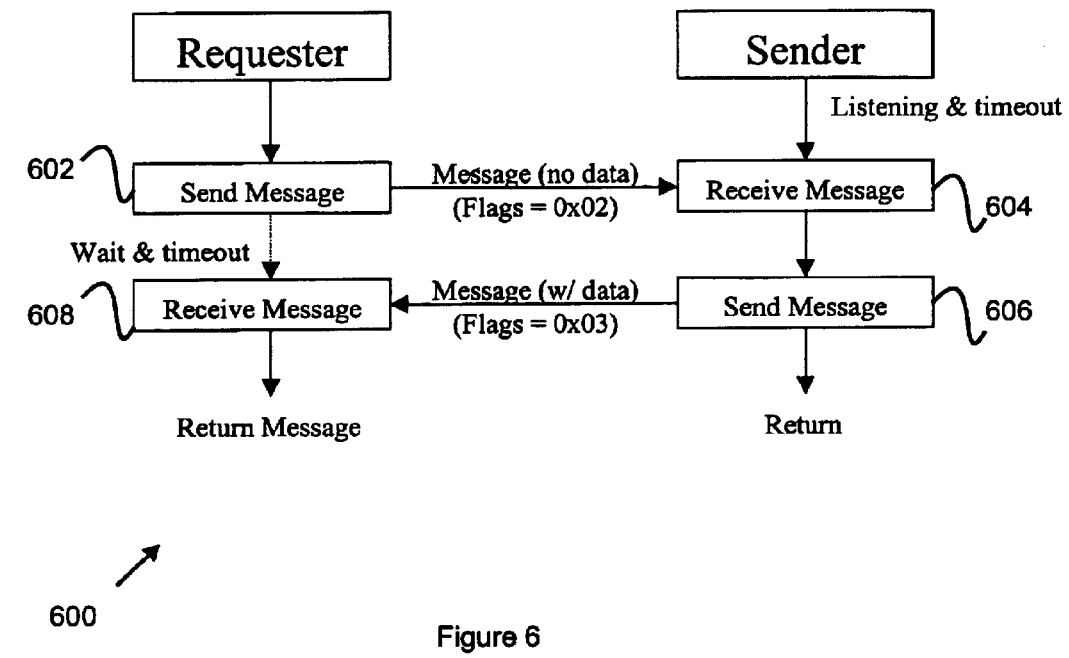
FIG. 6 depicts a flow diagram for receiving data according to a diagnostic imaging system communication protocol.

The Code field 406 of the message header 402 represents the message code that is common to both imaging and navigation computers. The Type field 408 represents a type that is a variation on the message code. The Flag field 410 represents the message flags that are used by the imaging and navigation computers to resolve the necessary action to be taken for each message. The specific cases of sending data versus requesting data are illustrated in FIGS. 5 and 6, respectively. For every message received, the returned message preferably has the same code as the sent message and the flags are incremented by one (reply flag is set high). The Status field 412 is used by the reply to indicate error conditions. The Data Length field 414 specifies the length of data following the header.

The Data Length field 414 is encoded big endian (encoded with the most significant byte first, to the least significant last) or little endian (encoded with the least significant byte first, to the most significant last). The Endian flag (bit 2 in the Flag field 410) specifies the endian encoding used for the rest of the message. This includes the Data Length field 414 in the message header 402 and any fields over one byte in the data field 404 of the message 400. With the use of the endian flag, the image data can be sent in the "endian" native to a particular machine without byte swapping each pixel greater than one byte in an image.

Turning briefly to FIG. 5, that figure illustrates a flow diagram 500 for sending data according to the diagnostic imaging system communication protocol. At step 502, the sender sends data (after formatting the header according to the header format 400) to a receiver. The receiver (which has been waiting and listening for a message) receives the data at step 504. The receiver responds at step 506 by sending an appropriate reply to the sender (formatted according to the header format 400, with the Flag field set as noted above). At step 508, the sender receives the reply and checks the status set by the receiver.

Similarly in FIG. 6, a flow diagram 600 for receiving data according to the diagnostic imaging system communication protocol is shown. At step 602, the sender sends a data request message (after formatting the header according to the header format 400) to the receiver. The receiver receives the message at step 604 and responds at step 508 by retrieving the requested data and sending an appropriate reply message (with the data) to the sender (formatted according to the header format 400, with the Flag field set as noted above). At step 508, the sender receives the reply message and may process or otherwise use the data provided in the reply message.

The messages are distributed into four general classifications: Event, Update Patient, Request Image, and Request Configuration classifications as shown in Table 3 below.

TABLE 3

| Message | Description | Code | Flags |
| --- | --- | --- | --- |
| Event | Send an event, e.g., Fluoro, New Exam, Ping (no-data) | 1 | 0 |
| Update Patient | Imaging computer 112 sends patient information to Navigation computer 108 (data) | 2 | 0 |
| Request Image | Navigation computer 108 requests an image from Imaging computer 112 (data in reply) | 3 | 2 |
| Request Configuration | Navigation computer 108 requests configuration from Imaging computer 112 (data in reply) | 4 | 2 |

Exemplary messages for use with the communication protocol are set forth below. Note that the first 8 bytes (0–7) of the message constitute the header (code, type, flags, status, and the data length) as shown in FIG. 4.

Name: Event
Description: Send an event to the peer
Message Direction: Bi-directional
Data Format: See below
Header:
Byte 0: Code (1)
Byte 1: Type (see Table 4)

TABLE 4

| Type | Description |
| --- | --- |
| 1 | Ping (no-operation) |
| 2 | Imaging (e.g., Fluoro) Begin |
| 3 | Imaging (e.g., Fluoro) End |
| 4 | New Exam |

Figure 7:
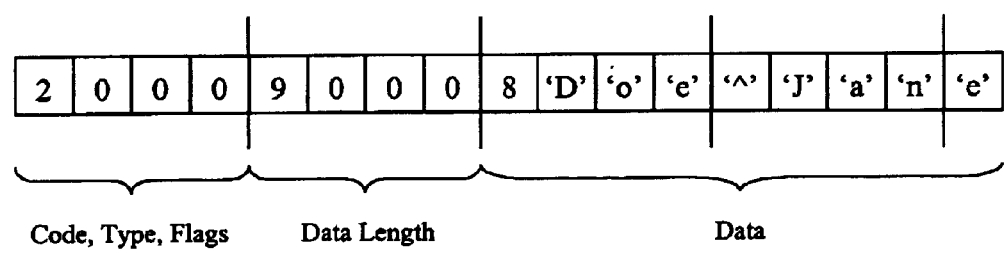
FIG. 7 shows the format for transmitting the patient name of "Jane Doe" to a navigation computer.

Byte 2: Flags (initial=0, reply=1)
Byte 3: Status (0)
Byte 4–7 Data Length (0)
Data: None.
Name: Update Patient
Description: Send the patient data to the Navigation computer
Message Direction: Imaging computer to Navigation computer
Data Format: A concatenation of the patient fields where the first byte is the length of the field to follow. The patient fields are grouped, for example, in the following order: patient name, birth date, sex, patient ID, physician name, procedure, and accession number. The name encoding may be that used by the DICOM standard, Part 5, Section 6.2 Value Representation. For example, a patient name of "Jane Doe" would be sent as shown in FIG. 7.
Header:
Byte 0: Code (2)
Byte 1: Type (0)
Byte 2: Flags (initial=0, reply=1)
Byte 3: Status (initial=0, reply=see Table 5)

TABLE 5

| Status | Description |
| --- | --- |
| 0 | OK |
| 1 | ERROR |

Byte 4–7 Data Length (initial=data payload size in bytes, reply=0)
Data (initial message only):
Bytes 8-end: Concatenation of the patient fields
Each field is a preferably string of ASCII characters prefixed by a byte indicating the length:
Patient Name—This field consists of three components in the following order of occurrence: a) Family Name, b) Given Name, c) Middle Name. The components are delimited by the caret '^' character. Interior null components require delimiters.
Trailing null components, including delimiters, may be omitted.
Birth Date, e.g., a Text string
Sex, e.g., a Text string (typically 'M' or 'F')
Patient ID, e.g., a Text string
Physician Name, e.g., using the same encoding as Patient Name
Procedure, e.g., a Text string
Accession Number, e.g., a Text string
Name: Request Image (and Reply)
Description: Request an image from the Workstation computer Message Direction: from the navigation computer to the imaging computer Data Format: An invalid image (test pattern, recalled image, or swap) is notified by an error in the reply message status. No data follows. A valid image is returned with a data payload.

Header:
Byte 0: Code (3)
Byte 1: Type (see Table 6)

TABLE 6

| Type | Description |
| --- | --- |
| 1 | Left Display, 980 × 980 × 8-bit (typically used) |
| 2 | Right Display, 980 × 980 × 8-bit |
| 3 | Filter Memory, 980 × 980 × 12-bit |
| 4 | Image Memory, 980 × 980 × 12-bit |
| 5 | Mask, 980 × 980 × 12-bit |

Byte 2: Flags (initial=2, reply=3)
Byte 3: Status (initial=0, reply, see Table 7)

TABLE 7

| Status | Description |
| --- | --- |
| 0 | OK - image valid |
| 1 | INVALID - image is invalid i.e. test pattern, recalled image, or swap |

Byte 4–7 Data Length (initial=0, reply=data payload size in bytes)
Data (reply only):

| | |
| --- | --- |
| Bytes 8–9: | Image header length - offset from here, byte 8, to the image data |
| | The value is typically 12 unless a different alignment of image data is needed. (16-bit unsigned integer) |
| Bytes 10–11: | Image width in pixels (16-bit unsigned integer) |
| Bytes 12–13: | Image height in pixels (16-bit unsigned integer) |
| Byte 14: | Bytes per pixel allocated, typically 1 or 2 (8-bit unsigned integer) |
| Byte 15: | Bits per pixel stored, assumes LSB at bit 0 (8-bit unsigned integer) |
| Byte 16: | Image flags that specify image features:<br>Bit 0: Negation (1: yes, 0: no)<br>Bit 1: Subtraction (1: yes, 0: no)<br>Bit 2: Flip Backward (1: yes, 0: no)<br>Bit 3: Flip Upside-down (1: yes, 0: no)<br>Bits 4–5: Magnification Mode (10: 2x, 01: 1x, 00: norm)<br>Bit 6–7: Reserved |
| Byte 17: | Reserved |
| Bytes 18–19: | Degrees of Rotation 0–360 (16-bit unsigned integer) |
| | Flip is applied before rotation transform |
| Bytes start-end: | Image data - The start is determined from Header Length (bytes 8–9). |

The image data length is determined by multiplying the image width, height, and bytes per pixel allocated.

Name: Request Configuration (and Reply)
Description: Request configuration information from the Workstation
Message Direction: from the navigation computer to the imaging computer
Data Format: See below.
Header:
Byte 0: Code (4)
Byte 1: Type (0)
Byte 2: Flags (initial=2, reply=3)
Byte 3: Status (initial=0, reply=see Table 8)

TABLE 8

| Status | Description |
| --- | --- |
| 0 | OK |
| 1 | ERROR |

Byte 4–7 Data Length (initial=0, reply=data payload size in bytes)
Data (reply only):
Bytes 8-end: Concatenation of the configuration fields
Each field is preferably a string of ASCII characters prefixed by a byte indicating the length. All data fields combined will not exceed 512 bytes total.
System—(e.g. "9800")
Image Intensifier Diameter—(e.g. "9", or "12")
Software Version—(e.g. "PN180130-08 7.1.2") The software version will preferably contain two numbers delimited by the under-bar '_' character. The first number is the OEC part number for the software (PN180130-08. The second number after the '_' is the version (7.1.2).

A magnification mode message is also defined to communicate the current magnification mode of an X-ray detector (e.g., an image intensifier). To that end, as examples, the magnification mode may specify one of a 12 inch, 9 inch, and 6 inch magnification mode for a 12 inch image intensifier or one of a 9 inch, 6 inch, and 4.5 inch magnification mode for a 9 inch image intensifier. Thus, the present imaging system allows navigation in several different magnification modes.

In particular, the Image End message may be used to synchronize image acquisition and coordinate determination. The command and control information provided over the network interfaces 206, 208, 214 allows the imaging computer 112 to inform the navigation computer 108 that image acquisition just completed. At that instant in time, the navigation computer 108 may obtain coordinate information from the x ray detector tracking sensor input port 116 to locate the image without intervening C-arm 130 movement and associated location error.

Thus, the present integrated fluoroscopic surgical navigation and imaging workstation provides a high speed digital communication interface between the navigation subsystem and the imaging subsystem, as well as a bi-directional command and control interface. As a result, full resolution digital images are quickly transferred, and the navigation system is coordinated with the imaging system to maintain accurate tracking of surgical tools. Furthermore, the present command protocol provides a standard communication protocol that may be used by any supporting navigation system to communication with any supporting imaging system. Additional components required by "Add-on" type systems (e.g., carts, monitors, monitor arms, power supplies, cabling, and the like) are eliminated, resulting in less crowding in the operating environment.

While the invention has been described with reference to a preferred embodiment, those skilled in the art will understand that various changes may be made and equivalents may be substituted without departing from the scope of the invention. In addition, many modifications may be made to adapt a particular step, structure, or material to the teachings of the invention without departing from its scope. Therefore, it is intended that the invention not be limited to the particular embodiment disclosed, but that the invention will include all embodiments falling within the scope of the appended claims.

What is claimed is:

1. A medical diagnostic imaging system comprising:
   an X-ray source and X-ray detector;
   a surgical instrument;
   sensors tracking a position of at least one of said surgical instrument and said X-ray detector by outputting signals;
   an imaging and navigation workstation including an imaging subsystem executing fluoroscopic imaging based on an output of said X-ray detector and a navigation subsystem tracking a signal from at least one of said sensors, wherein the signal is representative of a position of at least one of said surgical instrument and said X-ray detector with respect to a coordinate system;
   a private digital communication interface bi-directionally coupling said imaging subsystem to said navigation subsystem to help accomplish at least synchronization of image acquisition and coordinate determination; and
   a display for displaying fluoroscopic images superimposed with a displayed instrument such that a relation of said displayed instrument with respect to said fluoroscopic image corresponds to a relation of said surgical instrument to a patient.

2. The medical diagnostic imaging system of claim 1 wherein command and control information is sent between said imaging subsystem and said navigation subsystem over said digital communication interface to coordinate imaging and navigation functions.

3. The medical diagnostic imaging system of claim 1 wherein imaging information is sent from said imaging subsystem to said navigation subsystem over said digital communication interface.

4. The medical diagnostic imaging system of claim 1 wherein imaging information and command and control information are sent between said imaging subsystem and said navigation subsystem over said digital communication interface.

5. The medical diagnostic imaging system of claim 1 wherein said digital communication interface comprises a network.

6. The medical diagnostic imaging system of claim 1 wherein said navigation subsystem and said imaging subsystem are electrically and mechanically integrated in said workstation.

7. The medical diagnostic imaging system of claim 1 further comprising a tracker module comprising an input receiving surgical instrument tracking signals from said sensors.

8. The medical diagnostic imaging system of claim 1 further comprising a tracker module comprising an input receiving detector tracking signals from said sensors.

9. The medical diagnostic imaging system of claim 1, wherein said imaging and navigation subsystems are placed within a self-contained mobile cart system.

10. A medical diagnostic imaging system comprising:
    a surgical instrument;
    an X-ray source and X-ray detector,
    sensors tracking a position of at least one of said surgical instrument and said X-ray detector, wherein each of said sensors outputs a pulsed signal;
    an imaging and navigation workstation including an imaging subsystem executing fluoroscopic imaging based on an output of said X-ray detector and a navigation subsystem tracking pulsed signals from said sensors representative of positions of said surgical instrument and said X-ray detector with respect to a coordinate system;
    a private network, internal to said imaging system, coupling said imaging subsystem to said navigation subsystem to help accomplish at least synchronization of image acquisition and coordinate determination; and
    a display for displaying fluoroscopic images superimposed with a displayed instrument such that a relation of said displayed instrument with respect to said fluoroscopic image corresponds to a relation of said surgical instrument to a patient.

11. The diagnostic imaging system of claim 10 wherein said network provides bi-directional communication between said imaging subsystem and said navigation subsystem.

12. The diagnostic imaging system of claim 10 wherein said network comprises a digital communication interface between said imaging subsystem and said navigation subsystem.

13. The medical diagnostic imaging system of claim 10 wherein command and control information is sent between said imaging subsystem and said navigation subsystem over said network to coordinate imaging and navigation functions.

14. The medical diagnostic imaging system of claim 10 wherein imaging information is sent from said imaging subsystem to said navigation subsystem over said network.

15. The medical diagnostic imaging system of claim 10 wherein imaging information and command and control information are sent between said imaging subsystem and said navigation subsystem over said network.

16. The medical diagnostic imaging system of claim 10 wherein said network comprises an Ethernet connection supporting at least one of 10BaseT throughput and 100BaseT throughput.

17. The medical diagnostic imaging system of claim 10 wherein said imaging subsystem and said navigation subsystem communicate over said network using TCP/IP protocol employing IP addressing schemes.

18. The medical diagnostic imaging system of claim 10, wherein said imaging and navigation subsystems are placed within a self-contained mobile cart system.

* * * * *